(12) United States Patent
Vogelbaum et al.

(10) Patent No.: US 9,907,941 B2
(45) Date of Patent: *Mar. 6, 2018

(54) CONVECTION ENHANCED DELIVERY DEVICE AND SYSTEM

(71) Applicant: THE CLEVELAND CLINIC FOUNDATION, Cleveland, OH (US)

(72) Inventors: Michael A. Vogelbaum, Moreland Hills, OH (US); Shengqiang Gao, Beachwood, OH (US); William Kolosi, Stow, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 272 days.

This patent is subject to a terminal disclaimer.

(21) Appl. No.: 14/804,427

(22) Filed: Jul. 21, 2015

(65) Prior Publication Data

US 2016/0015930 A1  Jan. 21, 2016

Related U.S. Application Data

(60) Provisional application No. 62/026,945, filed on Jul. 21, 2014.

(51) Int. Cl.
*A61M 25/00* (2006.01)
*A61M 37/00* (2006.01)
*A61M 25/02* (2006.01)

(52) U.S. Cl.
CPC ............ *A61M 37/00* (2013.01); *A61M 25/00* (2013.01); *A61M 2025/0031* (2013.01);
(Continued)

(58) Field of Classification Search
CPC .................. A61M 37/00; A61M 25/00; A61M 2025/0031; A61M 2210/0693;
(Continued)

(56) References Cited

U.S. PATENT DOCUMENTS 6,302,141 B1   10/2001   Markulec et al.
6,623,457 B1   9/2003    Rosenberg
(Continued)

FOREIGN PATENT DOCUMENTS

EP    2060287 A1    5/2009
WO    03066123 A2   8/2003
(Continued)

OTHER PUBLICATIONS

International Search Report and Written Opinion for PCT/US2015/041249, dated Oct. 9, 2015, pp. 1-20.

*Primary Examiner* — Kevin C Sirmons
*Assistant Examiner* — Amber Stiles
(74) *Attorney, Agent, or Firm* — Tarolli, Sundheim, Covell & Tummino LLP

(57) ABSTRACT

A convection enhanced delivery device comprises a support member and an elongated microcatheter carried by the support member. The microcatheter projects lengthwise away from the support member. The microcatheter includes a catheter lumen extending in a first direction. A fluid conduit carried by the support member. The fluid conduit includes a conduit lumen that extends in a second direction different than the first direction. The conduit lumen is in fluid communication with the catheter lumen. An inlet port and a connecting port are also carried by the support member. The inlet port is in fluid communication with the fluid conduit. The connecting port is separate from the inlet port and is in fluid communication with the fluid conduit. The connecting port is configured to engage an end portion of an external fluid conduit such that the external fluid conduit projects away from the connecting port and from the support member.

20 Claims, 5 Drawing Sheets

(52) U.S. Cl.
CPC .............. *A61M 2025/0042* (2013.01); *A61M 2025/028* (2013.01); *A61M 2205/04* (2013.01); *A61M 2210/0693* (2013.01)

(58) Field of Classification Search
CPC ........ A61M 2205/04; A61M 2025/028; A61M 2025/0042; A61M 25/02
See application file for complete search history.

(56) References Cited

U.S. PATENT DOCUMENTS

| | | |
|---|---|---|
| 8,257,324 B2 | 9/2012 | Prausnitz et al. |
| 2003/0045866 A1 | 3/2003 | Petersen |
| 2004/0215173 A1 | 10/2004 | Kunst |
| 2008/0243082 A1* | 10/2008 | Goodman .............. A61M 25/02 604/180 |
| 2009/0187149 A1* | 7/2009 | Nelson .............. A61M 39/0247 604/175 |
| 2010/0217196 A1* | 8/2010 | Nelson .................. A61M 5/141 604/174 |
| 2010/0280494 A1 | 11/2010 | Matsuura et al. |
| 2012/0310182 A1 | 12/2012 | Fielder et al. |
| 2013/0035560 A1 | 2/2013 | Anand et al. |
| 2014/0171760 A1 | 6/2014 | Singh et al. |
| 2016/0136411 A1* | 5/2016 | Vogelbaum ........... A61M 25/00 604/513 |

FOREIGN PATENT DOCUMENTS

| | | |
|---|---|---|
| WO | 2007093778 A1 | 8/2007 |
| WO | 2008020967 A2 | 2/2008 |
| WO | 2008100930 A2 | 8/2008 |
| WO | 2008115566 A2 | 9/2008 |
| WO | 2011098768 A1 | 8/2011 |

* cited by examiner

CONVECTION ENHANCED DELIVERY DEVICE AND SYSTEM

RELATED APPLICATION

This application claims priority to U.S. Provisional Patent Application Ser. No. 62/026,945 filed Jul. 21, 2014, the entire content of which is hereby incorporated by reference.

FIELD OF THE INVENTION

The present invention relates to a convection enhanced delivery device that comprises a microcatheter and a fluid conduit carried by a support member and, more particularly, to a convection enhanced delivery device that comprises a microcatheter carried by a support member and in fluid communication with a fluid conduit embedded in the support member.

BACKGROUND OF THE INVENTION

Convection enhanced delivery ("CED") of a bioactive agent involves introducing a fluid containing the bioactive agent into a patient's tissue under pressure so that the fluid moves through the tissue via bulk flow. Implementing CED generally involves inserting multiple catheters into the tissue to be treated, such as cerebral tissue. To reduce the risk of hemorrhage and/or trauma to the tissue and to reduce the risk of backflow (i.e., non-delivery into tissue parenchyma), it is desirable for the catheters to be microcatheters with small outside diameters.

SUMMARY OF THE INVENTION

The present invention is directed to a convection enhanced delivery device that comprises a microcatheter and a fluid conduit carried by a support member and, more particularly, to a convection enhanced delivery device that comprises a microcatheter carried by a support member and in fluid communication with a fluid conduit embedded in the support member.

In accordance with an embodiment of the present invention, a convection enhanced delivery device comprises a support member and an elongated first microcatheter carried by the support member. The first microcatheter has a length and projects lengthwise away from the support member such that a proximal end of the first microcatheter is disposed adjacent the support member and an opposite distal end of the first microcatheter is spaced apart from the support member. The first microcatheter includes a first catheter lumen extending in a first direction lengthwise of the microcatheter. The convection enhanced delivery device also comprises a first fluid conduit carried by the support member. The first fluid conduit includes a first conduit lumen. The first conduit lumen extends in a second direction different than the first direction. The first conduit lumen is in fluid communication with the first catheter lumen. The convection enhanced delivery device further comprises an inlet port carried by the support member and a connecting port carried by the support member. The inlet port is in fluid communication with the first conduit. The connecting port is separate from the inlet port and is in fluid communication with the first conduit. The connecting port is configured to engage an end portion of an external fluid conduit such that the external fluid conduit projects away from the connecting port and from the support member.

In accordance with another embodiment of the invention, a kit of components for a convection enhanced delivery system comprises at least two convection enhanced delivery devices and at least one external fluid conduit for interconnecting the at least two convection enhanced delivery devices. Each convection enhanced delivery device comprises a support member and an elongated microcatheter carried by the support member. The microcatheter has a length and projects lengthwise away from the support member such that a proximal end of the microcatheter is disposed adjacent the support member and an opposite distal end of the microcatheter is spaced apart from the support member. The microcatheter includes a catheter lumen extending in a first direction lengthwise of the microcatheter. The convection enhanced delivery device also comprises a first fluid conduit carried by the support member. The first fluid conduit includes a conduit lumen. The conduit lumen extends in a second direction different than the first direction. The conduit lumen is in fluid communication with the catheter lumen. The convection enhanced delivery device further comprises an inlet port carried by the support member and a connecting port carried by the support member. The inlet port is in fluid communication with the first conduit. The connecting port is separate from the inlet port and is in fluid communication with the first conduit. The connecting port is configured to engage an end portion of an external fluid conduit such that the external fluid conduit projects away from the connecting port and from the support member.

In accordance with a further embodiment of the invention, a convection enhanced delivery system comprises an external fluid conduit and first and second convection enhanced delivery devices. The first convection enhanced delivery device comprises a first support member and an elongated first microcatheter carried by the first support member. The first microcatheter has a length and projects lengthwise away from the first support member such that a proximal end of the first microcatheter is disposed adjacent the first support member and an opposite distal end of the first microcatheter is spaced apart from the first support member. The first microcatheter includes a first catheter lumen extending in a first direction lengthwise of the first microcatheter. The first convection enhanced delivery device also comprises a first fluid conduit carried by the first support member. The first fluid conduit includes a first conduit lumen. The first conduit lumen extends in a second direction different than the first direction and is in fluid communication with the first catheter lumen. The first convection enhanced delivery device further comprises a first inlet port carried by the first support member and a first connecting port carried by the first support member and separate from the first inlet port. The first inlet port and the first connecting port are in fluid communication with the first fluid conduit. The first connecting port is configured to engage a first end portion of the external fluid conduit such that the external fluid conduit projects away from the first connecting port and from the first support member. The second convection enhanced delivery device comprises a second support member and an elongated second microcatheter carried by the second support member. The second microcatheter has a length and projects lengthwise away from the second support member such that a proximal end of the second microcatheter is disposed adjacent the second support member and an opposite distal end of the second microcatheter is spaced apart from the second support member. The second microcatheter includes a second catheter lumen extending in a third direction lengthwise of the second microcatheter. The second convection enhanced delivery device also comprises a second fluid conduit carried by the second support member. The second fluid conduit includes a second conduit lumen. The second conduit lumen extends in a fourth direction different than the third direction and is in fluid communication with the second catheter lumen. The second convection enhanced delivery device further comprises a second inlet port carried by the second support member and a second connecting port carried by the second support member and separate from the second inlet port. The second inlet port and the second connecting port are in fluid communication with the second fluid conduit. The second connecting port engages a second end portion of the external fluid conduit such that the external fluid conduit projects away from the second connecting port and from the second support member.

In accordance with yet a further embodiment of the invention, a convection enhanced delivery system comprises a first convection enhanced delivery device and a mesh support structure. The first convection enhanced delivery device comprises a first support member and an elongated first microcatheter carried by the first support member. The first microcatheter has a length and projects lengthwise away from the first support member such that a proximal end of the first microcatheter is disposed adjacent the first support member and an opposite distal end of the first microcatheter is spaced apart from the first support member. The first microcatheter includes a first catheter lumen extending in a first direction lengthwise of the first microcatheter. The mesh support structure defines openings through the mesh support structure. The mesh support structure is configured and dimensioned to support the first support member of the first convection enhanced delivery device while permitting the first microcatheter carried by the first support member to extend through at least one of the openings defined in the mesh support structure.

BRIEF DESCRIPTION OF THE DRAWINGS

The foregoing and other features and advantages of the present invention will become apparent to one skilled in the art upon consideration of the following description of the invention and the accompanying drawings, in which.

DETAILED DESCRIPTION

Figure 1:
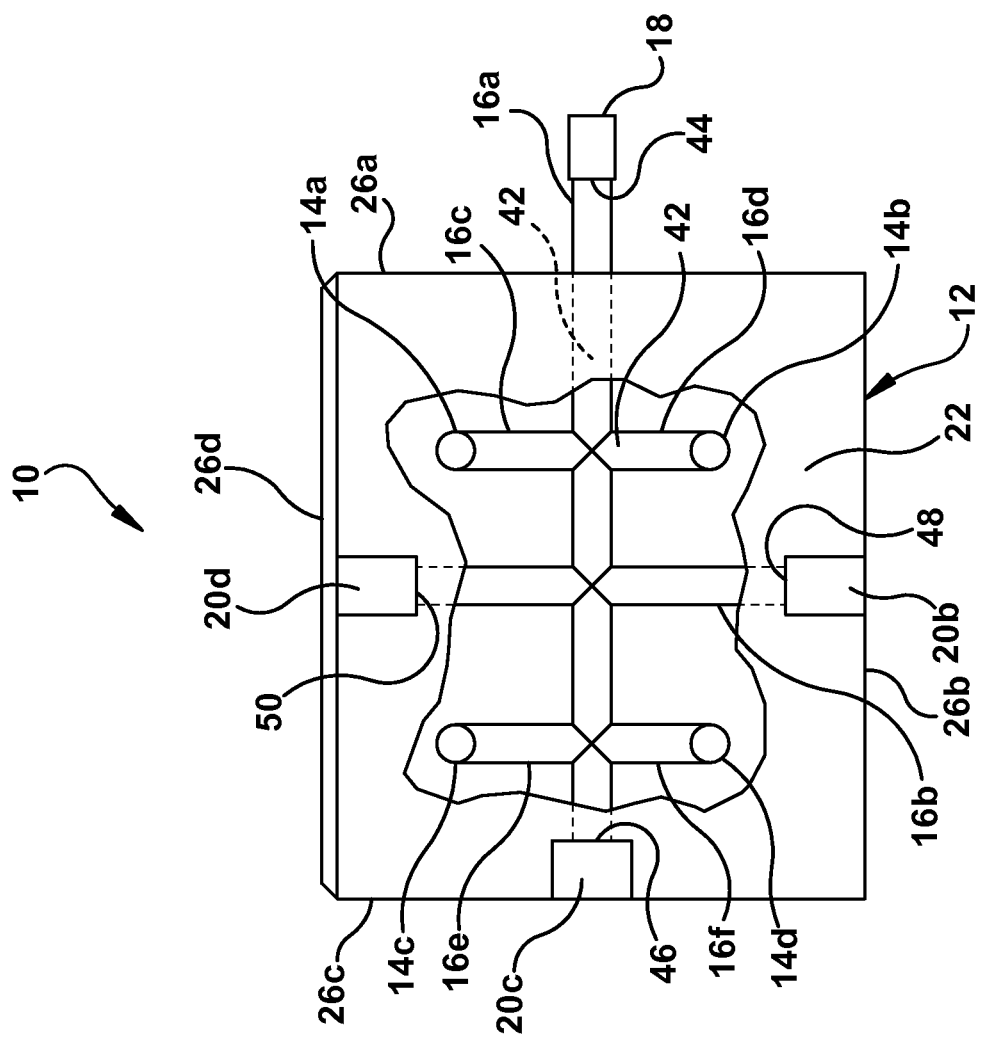
FIG. 1 is a schematic top view of a convection enhanced delivery device in accordance with the present invention.
Figure 2:
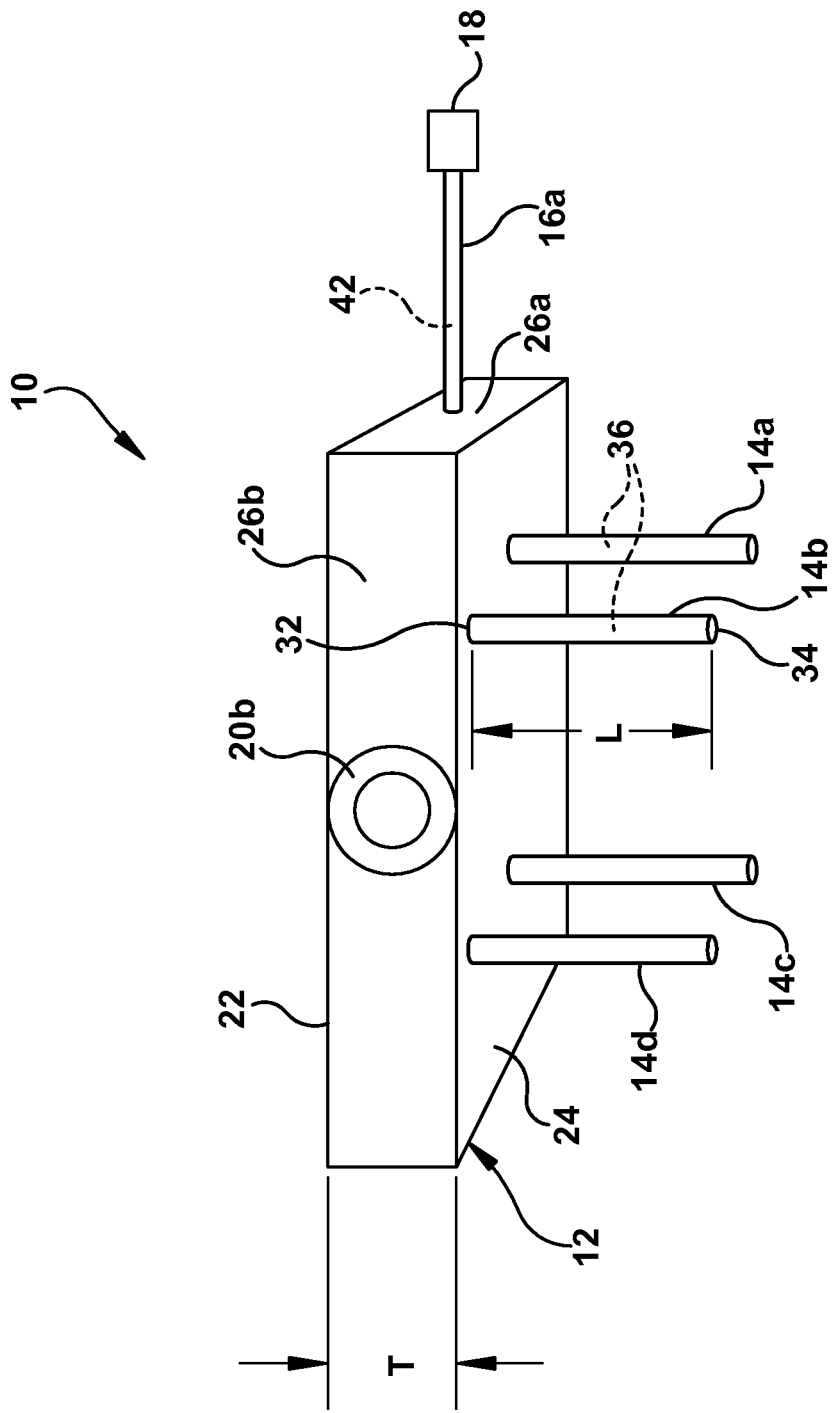
FIG. 2 is a perspective view of the convection enhanced delivery device of FIG. 1.

FIGS. 1 and 2 illustrate a convection enhanced delivery device 10, in accordance with an example of the present invention. The convection enhanced delivery device 10 includes a platform, substrate or support member 12, a plurality of microcatheters 14, a plurality of fluid conduits 16, an inlet port 18, and plurality of connecting ports 20. The microcatheters 14, the fluid conduits 16, the inlet port 18, and the connecting ports 20 are supported by or carried by the support member 12. The microcatheters 14, the fluid conduits 16, the inlet port 18, and the connecting ports 20 are also fluidly connected to or in fluid communication with one another.

The substrate or support member 12 supports or carries the microcatheters 14, the fluid conduits 16, the inlet port 18, and the connecting ports 20. As illustrated in FIGS. 1 and 2, the support member 12 is generally square in shape and has a first major surface 22 and an opposite second major surface 24. The first and second major surfaces extend parallel to one another and are spaced apart from one another by a distance that is the thickness "T" of the support member 12. The thickness "T" is sufficient to permit the fluid conduits 16 and the connecting ports 20 to be embedded in the support member 12. The support member also has four side surfaces 26. Each side surface 26 extends along a different one of the four sides of the support member 12 and also extends from the first major surface 22 to the second major surface 24.

The support member 12 is made of a biocompatible material, such as a medical grade silicone. The support member 12 of FIGS. 1 and 2 and the material of which the support member is made are flexible. As used in this application, "flexible" means that a structure or material, such as the support member 12 or the material of which the support member is made, is capable of being flexed, which is to say capable of being turned, bowed, or twisted without breaking. The flexibility of the support member 12 is sufficient to permit a surgeon or other health care provider to bend the support member so that it both generally conforms to the contour of a patient's tissue (not shown) and also maintains such conformity after being placed in contact with the patient's tissue. As a result, the second major surface 24 of the support member 12 may be positioned in substantially complete surface contact with a patient's tissue so as to help provide a barrier against backflow of fluid delivered to the patient's tissue by the microcatheters 14. When positioned in "substantially complete surface contact" with a patient's tissue, the second major surface 24 has a degree of surface contact that is as complete as practical to help provide a barrier against backflow without unduly lengthening or otherwise degrading the process of implanting the support member in a patient's tissue.

Although the support member 12 is shown with a square shape, the support member may have any shape, including, for example, rectangular or circular. The support member 12 may also be relatively rigid, rather than flexible, if the circumstances of its use by a surgeon or other health care provider indicate that a relatively rigid support member would be desirable. The thickness "T" of the support member 12 may also be larger or smaller than shown in FIGS. 1 and 2 in comparison, for example, to the diameters of the fluid conduits 16 or of the connecting ports 20.

The microcatheters 14 project from the second major surface 24 of the support member 12. Each microcatheter 14 is an elongated hollow tube and has a first end 32 and an opposite second end 34. The longest dimension of each microcatheter 14 is a length "L" that extends from the first end 32 of the microcatheter to the second end 34. The first end 32 of each microcatheter 14 is proximal to the support member 12 and is disposed adjacent the support member 12. More specifically, the first end 32 either abuts the second major surface 24 of the support member 12 or is disposed within the support member. The second end 34 of each microcatheter 14 is distal to the support member 12 and is spaced apart from the support member 12 by the length "L" of the microcatheter, to the extent the microcatheter is not embedded in the support member at the first end 32. Each microcatheter 14 is attached, connected, secured or coupled to the support member 12 at or adjacent to the first end 32 of the microcatheter. Attaching, connecting, securing or coupling each microcatheter 14 to the support member 12 may be accomplished, for example, by using an adhesive, by embedding the first end 32 of the microcatheter in the support member, or by joining the microcatheter to another structure, such as one of the fluid conduits 16, that is attached, connected, secured or coupled to the support member. The microcatheters 14 are thus supported or carried by the support member 12.

Four microcatheters 14a, 14b, 14c, and 14d are shown in FIGS. 1 and 2 arranged in a square pattern. More or fewer microcatheters 14 may be included in the convection enhanced delivery device 10. The microcatheters 14 may also be arranged in a pattern other than a square. Each microcatheter 14 has a catheter lumen 36 that extends along a central longitudinal axis of the microcatheter lengthwise of the microcatheter. The catheter lumen 36 has length equal to the length "L" of the microcatheter 14. Each microcatheter 14 is formed of a biocompatible material, such as polytetrafluoroethylene ("PTFE"), that is sufficiently rigid to penetrate a patient's tissue and that is also sufficiently flexible and resilient to withstand being deflected and then return to a non-deflected position. As used in this application, "resilient" means that a structure or material, such as a microcatheter 14 or material of which the microcatheter is made, is capable of returning freely to a previous position, shape or condition, which is to say capable of recovering its size and shape after deformation. The second end 34 of each microcatheter 14 may be sharpened or pointed to facilitate inserting the microcatheter into a patient's tissue.

The fluid conduits 16 are hollow tubes supported or carried by the support member 12. As shown, the fluid conduits 16 are fully embedded in the support member 12 such that the external circumferential surfaces of the fluid conduits 16 are completely covered by the support member. The fluid conduits 16 may alternatively be only partially embedded in or covered by the support member 12. As another alternative, the fluid conduits 16 may simply lie on the first major surface 22 of the support member 12 and be secured to the support member by, for example, an adhesive.

Each fluid conduit 16 has a conduit lumen 42 that extends along a central longitudinal axis of the fluid conduit lengthwise of the fluid conduit. Each of the fluid conduits 16 and each of the conduit lumens 42 has a longest dimension or length oriented transverse to or, more specifically as shown, perpendicular to the length "L" of the microcatheters 14a-d. Each of the fluid conduits 16 and each of the conduit lumens 42 thus extends in a direction that is different than the direction in which the microcatheters 14a-d extend. Each fluid conduit 16 is formed of a flexible biocompatible material, such as a medical grade silicone. The flexibility of the fluid conduits 16 is sufficient to permit a surgeon or other health care provider to bend the support member 12 in which the fluid conduit embedded so that the support member both generally conforms to the contour of a patient's tissue (not shown) and also maintains such conformity after being placed in contact with the patient's tissue.

In the embodiment of FIG. 1, each of the fluid conduits 16 is a straight length of tube or tubing. Thus, as illustrated in FIG. 1, there is a central or first fluid conduit 16a that extends from a first side surface 26a of the support member 12 to an opposite second side surface 26c. A cross or second fluid conduit 16b extends from a third side surface 26b of the support member 12 to an opposite fourth side surface 26d. The second fluid conduit 16b is oriented perpendicular to the first fluid conduit 16a. The second fluid conduit 16b intersects and is fluidly connected to or in fluid communication with the first fluid conduit 16a.

Intermediate the first side surface 26a and the second fluid conduit 16b are two connecting fluid conduits or third and fourth fluid conduits 16c and 16d that extend from the first fluid conduit 16a to the first ends 32 of two different microcatheters 14a and 14b, respectively. The third and fourth fluid conduits 16c and 16d are fluidly connected to or in fluid communication with the first fluid conduit 16a and also with the microcatheter 14a and the microcatheter 14b, respectively. Intermediate the side surface 26c and the second fluid conduit 16b are two more connecting fluid conduits or fifth and sixth fluid conduits 16e and 16f that extend from the first fluid conduit 16a to the first ends 32 of two different microcatheters 14c and 14d, respectively. The fifth and sixth fluid conduits 16e and 16f are fluidly connected to or in fluid communication with the first fluid conduit 16a and also with the microcatheter 14c and the microcatheter 14d, respectively.

The first fluid conduit 16a extends through and beyond the first side surface 26a of the support member 12, to the right as viewed in FIG. 1. At the right end 44 of the first fluid conduit 16a, the inlet port 18 is joined to the first fluid conduit. The inlet port 18 is configured to engage an end portion of a first external fluid conduit (not shown in FIGS. 1 and 2) such that the external fluid conduit projects away from the inlet port 18 and from the support member 12. An external fluid conduit, such as the first external fluid conduit (not shown), is external to and separate from the support member 12, but may or may not be external to a patient's body or tissue. The inlet port 18 may be configured in any convenient manner, such as a Luer lock, that will provide an easily operable, yet securely retained, connection or engagement with the external fluid conduit to help prevent leakage of fluid at the inlet port.

At the opposite left end 46 of the first fluid conduit 16a, a connecting port 20c is joined to the first fluid conduit. As can be seen, the connecting port 20c is separate from the inlet port 18. The most distal surface of the connecting port 20c is disposed at the side surface 26c of the support member 12. The connecting port 20c is presented in a direction different than the direction in which the microcatheters 14a-d extend. The connecting port 20c is configured to engage an end portion of a second external fluid conduit (not shown in FIGS. 1 and 2) such that the second external fluid conduit projects away from the connecting port 20c and from the support member 12. The connecting port 20c may be configured in any convenient manner, such as a Luer lock, that will provide an easily operable, yet securely retained, connection or engagement with the second external fluid conduit to help prevent leakage of fluid at the port. The ends 44 and 46 of the first fluid conduit 16a may abut the inlet port 18 and the connecting port 20c, respectively, as shown, or the first fluid conduit may extend into the inlet port and the connecting port so that the ends 44 and 46 are located inside of or at the outer or distal ends of the inlet port and the connecting port.

At one end 48 of the second fluid conduit 16b, a connecting port 20b is joined to the second fluid conduit. As can be seen, the connecting port 20b is separate from the inlet port 18. The most distal surface of the connecting port 20b is disposed at the side surface 26b of the support member 12. The connecting port 20b is presented in a direction different than the direction in which the microcatheters 14*a-d* extend. The connecting port 20*b* is configured to engage an end portion of a third external fluid conduit (not shown in FIGS. 1 and 2) such that the third external fluid conduit projects away from the connecting port 20*b* and from the support member 12. The connecting port 20*b* may be configured in any convenient manner, such as a Luer lock, that will provide an easily operable, yet securely retained, connection or engagement with the third external fluid conduit to help prevent leakage of fluid at the connecting port.

At the opposite end 50 of the second fluid conduit 16*b*, a connecting port 20*d* is joined to the second fluid conduit. As can be seen, the connecting port 20*d* is separate from the inlet port 18. The most distal surface of the connecting port 20*d* is disposed at the side surface 26*d* of the support member 12. The connecting port 20*d* is presented in a direction different than the direction in which the microcatheters 14*a-d* extend. The connecting port 20*d* is configured to engage an end portion of a fourth external fluid conduit (not shown in FIGS. 1 and 2) such that the fourth external fluid conduit projects away from the connecting port 20*d* and from the support member 12. The connecting port 20*d* may be configured in any convenient manner, such as a Luer lock, that will provide an easily operable, yet securely retained, connection or engagement with the fourth external fluid conduit to help prevent leakage of fluid at the connecting port. The ends 48 and 50 of the second fluid conduit 16*b* may abut the connecting ports 20*b* and 20*d*, respectively, as shown, or the second fluid conduit may extend into the connecting ports so that the ends 48 and 50 are located inside of or at the outer or distal ends of the connecting ports.

As described above, the convection enhanced delivery device 10 of FIGS. 1 and 2 includes a plurality of fluid conduits 16*a* and 16*c-f* that are fluidly interconnected with or in fluid communication with one another and with the microcatheters 14*a*-14*d*. The convection enhanced delivery device 10 thereby provides a network of fluid pathways for delivery of a fluid bioactive material, such as a liquid pharmaceutical material, from the inlet port 18 to the distal or second ends 34 of the microcatheters 14*a-d* for therapeutic treatment of a patient's tissue. In the network of fluid pathways, a discrete individual fluid conduit 16*c*, 16*d*, 16*e*, or 16*f* leads to and connects with and delivers fluid to each individual microcatheter 14*a*, 14*b*, 14*c*, or 14*d*, respectively. In addition, the fluid conduits 16*a* and 16*b* of the convection enhanced delivery device 10 of FIGS. 1 and 2 are fluidly interconnected with or in fluid communication with one another and with the connecting ports 20*b-d*. The convection enhanced delivery device 10 thereby provides a network of fluid pathways for delivery of a fluid bioactive material, such as a liquid pharmaceutical material, from the inlet port 18 to the connecting ports 20*b-d* for delivery or transmission to other devices, such as other convection enhanced delivery devices 10, either via direct connection to such other devices or via external conduits (not shown in FIGS. 1 and 2).

Figure 3:
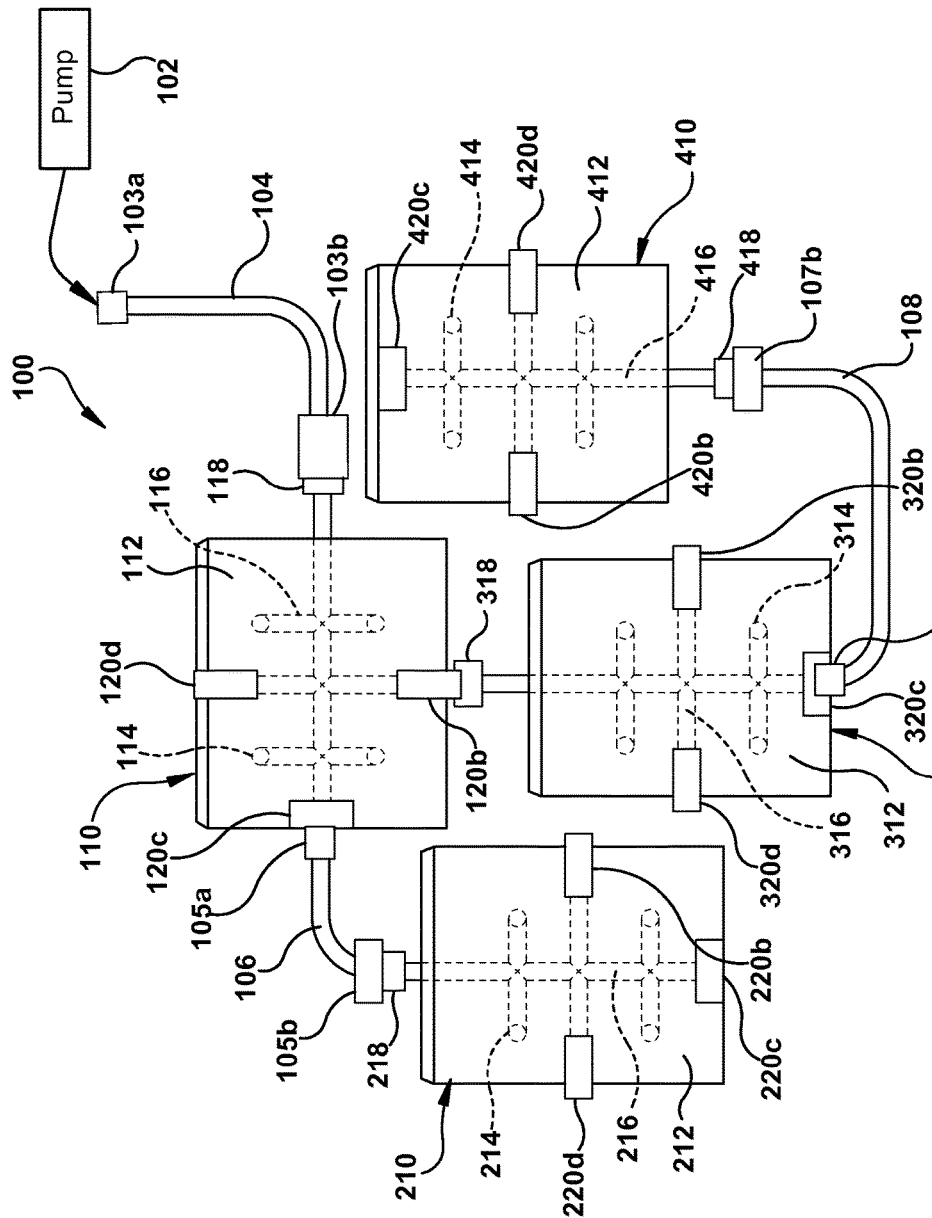
FIG. 3 is a schematic top view of a plurality of convection enhanced delivery devices as shown in FIG. 1, which are interconnected to form a convection enhanced delivery system in accordance with the present invention.

FIG. 3 illustrates an example of a convection enhanced delivery system 100 that comprises plural or multiple convection enhanced delivery devices 10 fluidly connected to or in fluid communication with one another. More particularly, as shown, the convection enhanced delivery system 100 comprises four convection enhanced delivery devices 110, 210, 310, and 410. Each of the convection enhanced delivery devices 110, 210, 310, and 410 is identical in shape, dimensions, and construction to each of other convection enhanced delivery devices and to the convection enhanced delivery device 10 of FIGS. 1 and 2. Accordingly, features or components of the convection enhanced delivery devices 110, 210, 310, and 410 corresponding to features or components of the convection enhanced delivery device 10 are identified with corresponding reference numerals increased by 100, 200, 300 or 400, depending upon which convection enhanced delivery device 110, 210, 310, or 410 is being described. Providing all the convection enhanced delivery devices 110, 210, 310, and 410 with same shape, dimensions, and construction will tend to reduce the manufacturing cost of the individual convection enhanced delivery devices and will also tend to facilitate the collection and production of a kit of parts or components to supply or provide to a surgeon or other health care provider. At the same time, however, the individual convection enhanced delivery devices 110, 210, 310, and 410 may have (a) support members 12 with different shapes and dimensions, (b) different numbers of microcatheters 14, (c) different numbers of connecting ports 20, (d) different numbers, shapes, or flow areas of fluid conduits 16, and/or (e) other differences in construction.

As illustrated in FIG. 3, the convection enhanced delivery system 100 is connected to a fluid source 102, such as a pump. The fluid source 102 is fluidly connected to or in fluid communication with a first external fluid conduit 104 for delivering or supplying a fluid bioactive material, such as a liquid pharmaceutical material, to the first external fluid conduit 104 and thus to the convection enhanced delivery system 100. The first external fluid conduit 104 has a central lumen and is formed of a flexible biocompatible material, such as a medical grade silicone. The flexibility of the first external fluid conduit 104 is sufficient to permit a surgeon or other health care provider to bend the first external fluid conduit as required to fit into the space available and also to maintain any bend imparted to the first external fluid conduit by the surgeon or other health care provider. The end of the first external fluid conduit 104 closest to the fluid source may have an attached port 103*a*, which may be configured in any convenient manner, such as a Luer lock, to provide an easily operable, yet securely retained, connection or engagement with the fluid source 102 to help prevent leakage of fluid at the port. The first external fluid conduit 104 may, for example, be tunneled subcutaneously from the port 103*a* so that only the port 103*a* is readily accessible after the convection enhanced delivery system 100 is fully implanted in a patient's tissue.

The end portion of the first external fluid conduit 104 opposite the port 103*a* is engaged with the inlet port 118 of the first convection enhanced delivery device 110. The end portion of the first external fluid conduit 104 engaged with the inlet port 118 may have an attached port 103*b*, which may be configured in any convenient manner, such as a Luer lock, to provide an easily operable, yet securely retained, connection or engagement with the inlet port 118 and thus the first convection enhanced delivery device 110 to help prevent leakage of fluid at the inlet port.

The first convection enhanced delivery device 110 includes three connecting ports 120*b*, 120*c*, and 120*d*. A second external fluid conduit 106 is engaged with the connecting port 120*c*. Like the first external fluid conduit 104, the second external fluid conduit 106 has a central lumen and is formed of a flexible biocompatible material, such as a medical grade silicone. The flexibility of the second external fluid conduit 106 is sufficient to permit a surgeon or other health care provider to bend the second external fluid conduit as required to fit into the space available and also to maintain any bend imparted to the second external fluid conduit by the surgeon or other health care provider. The end of the second external fluid conduit 106 closest to the first convection enhanced delivery device 110 may have an attached port 105a, which may be configured in any convenient manner, such as a Luer lock, to provide an easily operable, yet securely retained, connection or engagement with the connecting port 120c of the first convection enhanced delivery device 110 to help prevent leakage of fluid at the port.

The end portion of the second external fluid conduit 106 opposite the port 105a is engaged with the inlet port 218 of the second convection enhanced delivery device 210. The end portion of the second external fluid conduit 106 engaged with the inlet port 218 may have an attached port 105b, which may be configured in any convenient manner, such as a Luer lock, to provide an easily operable, yet securely retained, connection or engagement with the inlet port 218 and thus the second convection enhanced delivery device 210 to help prevent leakage of fluid at the port. The first convection enhanced delivery device 110 is thus fluidly connected to or in fluid communication with the second convection enhanced delivery device 210.

The connecting port 120b of the first convection enhanced delivery device 110 is engaged directly with the inlet port 318 of the third convection enhanced delivery device 310. The first convection enhanced delivery device 110 is thus fluidly connected to or in fluid communication with the third convection enhanced delivery device 310. There is no external fluid conduit connected or coupled between the connecting port 120b and the inlet port 318 of the third convection enhanced delivery device 310.

The connecting port 120d of the first convection enhanced delivery device 110 is blocked or closed with a plug (not shown) so that liquid cannot pass through the connecting port. If desired or required, however, the connecting port 120d may be engaged directly with the inlet port of another convection enhanced delivery device (not shown) or engaged with an external fluid conduit (not shown).

As described above, the inlet port 218 of the second convection enhanced delivery device 210 is engaged with the port 105b on one end portion of the second external fluid conduit 106 and is thus fluidly connected to or in fluid communication with the first convection enhanced delivery device 110. The second convection enhanced delivery device 210 includes three connecting ports 220b, 220c, and 220d. Each of the three connecting ports 220b, 220c, and 220d of the second convection enhanced delivery device 210 is blocked or closed with a plug (not shown) so that fluid cannot pass through the connecting port. If desired or required, however, one or more of the connecting ports 220b, 220c, and 220d may be engaged directly with the inlet port of another convection enhanced delivery device (not shown) or engaged with an external fluid conduit (not shown).

As also described above, the inlet port 318 of the third convection enhanced delivery device 310 is engaged directly with the connecting port 120b of the first convection enhanced delivery device 110. The third convection enhanced delivery device 310 includes three connecting ports 320b, 320c, and 320d. Each of the connecting ports 320b and 320d of the third convection enhanced delivery device 310 is blocked or closed with a plug (not shown) so that liquid cannot pass through the connecting port. If desired or required, however, one or more of the connecting ports 320b and 320d may be engaged directly with the inlet port of another convection enhanced delivery device (not shown) or engaged with an external fluid conduit (not shown).

A third external fluid conduit 108 is engaged with the connecting port 320c of the third convection enhanced delivery device 310. Like the first external fluid conduit 104 and the second external fluid conduit 106, the third external fluid conduit 108 has a central lumen and is formed of a flexible biocompatible material, such as a medical grade silicone. The flexibility of the third external fluid conduit 108 is sufficient to permit a surgeon or other health care provider to bend the second external fluid conduit as required to fit into the space available and also to maintain any bend imparted to the second external fluid conduit by the surgeon or other health care provider. The end of the third external fluid conduit 108 closest to the third convection enhanced delivery device 310 may have an attached port 107a, which may be configured in any convenient manner, such as a Luer lock, to provide an easily operable, yet securely retained, connection or engagement with the connecting port 320c of the third convection enhanced delivery device 310 to help prevent leakage of fluid at the port.

The end portion of the third external fluid conduit 108 opposite the port 107a is engaged with the inlet port 418 of the fourth convection enhanced delivery device 410. The end portion of the third external fluid conduit 108 engaged with the inlet port 418 may have an attached port 107b, which may be configured in any convenient manner, such as a Luer lock, to provide an easily operable, yet securely retained, connection or engagement with the inlet port 418 and thus the fourth convection enhanced delivery device 410 to help prevent leakage of fluid at the port. The third convection enhanced delivery device 310 is thus fluidly connected to or in fluid communication with the fourth convection enhanced delivery device 410.

As described above, the inlet port 418 of the fourth convection enhanced delivery device 410 is engaged with the port 107b on one end portion of the third external fluid conduit 108 and is thus fluidly connected to or in fluid communication with the third convection enhanced delivery device 310. The fourth convection enhanced delivery device 410 includes three connecting ports 420b, 420c, and 420d. Each of the three connecting ports 420b, 420c, and 420d of the fourth convection enhanced delivery device 410 is blocked or closed with a plug (not shown) so that fluid cannot pass through the connecting port. If desired or required, however, one or more of the connecting ports 420b, 420c, and 420d may be engaged directly with the inlet port of another convection enhanced delivery device (not shown) or engaged with an external fluid conduit (not shown).

As a result of the foregoing construction or assembly of the convection enhanced delivery system 100, fluid may flow from the fluid source 102, along the central lumen of the first external fluid conduit 104, along the conduit lumens of the fluid conduits 116 of the first convection enhanced delivery device 110, along the catheter lumens of the microcatheters 114 of the first convection enhanced delivery device, and out of the open distal ends of the microcatheters. Fluid may also flow along the conduit lumens of the fluid conduits 116, through the connecting port 120c, along the central lumen of the second external fluid conduit 106, along the conduit lumens of the fluid conduits 216 of the second convection enhanced delivery device 210, along the catheter lumens of the microcatheters 214 of the second convection enhanced delivery device, and out of the open distal ends of the microcatheters 214. Fluid may further flow along the conduit lumens of the fluid conduits 116, through the connecting port 120b, along the conduit lumens of the fluid conduits 316 of the third convection enhanced delivery device 310, along the catheter lumens of the microcatheters 314 of the third convection enhanced delivery device, and out of the open distal ends of the microcatheters 314. Fluid may yet further flow along the conduit lumens of the fluid conduits 316, through the connecting port 320c, along the conduit lumens of the conduits 416 of the fourth convection enhanced delivery device 410, along the catheter lumens of the microcatheters 414 of the fourth convection enhanced delivery device, and out of the open distal ends of the microcatheters 414.

In use, when the convection enhanced delivery system 100 is to be inserted into tissue, such as cerebral tissue, of a patient, a surgeon or other health care provider selects a convection enhanced delivery device, such as the first convection enhanced delivery device 110, from a kit of component parts (not shown). The kit of parts includes the first, second, third, and fourth convection enhanced delivery devices 110, 210, 310 and 410 and the first, second, and third external fluid conduits 104, 106, and 108. The kit of parts may also include additional convection enhanced delivery devices, additional external fluid conduits, and other devices and components that may be required or desired to provide a selected treatment for the patient's tissue. The kit of parts may, for example, include a sufficient number of convection enhanced delivery devices and external fluid conduits to ensure that the surgeon or other health care provider will have enough convection enhanced delivery devices to cover a majority of a wall of a resection cavity in a patient's brain tissue after removal of a tumor.

In one method of implanting the convection enhanced delivery system 100 into a patient's tissue, the surgeon or other health care provider implants the first convection enhanced delivery device 110 into the patient's tissue at a desired location by pressing the distal ends of the microcatheters 114 into the patient's tissue and generally conforming the support member 112 to the exposed surface of the patient's tissue. The surgeon or other health care provider then implants each of the second, third, and fourth convection enhanced delivery devices 210, 310, and 410 into the patient's tissue at desired locations by pressing the distal ends of the microcatheters 214, 314, and 414, respectively, into the patient's tissue and generally conforming the support members 212, 312, and 412, respectively, to the exposed surface of the patient's tissue. Thereafter, the surgeon or other health care provider interconnects the first, second, third, and fourth convection enhanced delivery devices 110, 210, 310, and 410 using external fluid conduits 106 and 108 and also direct connections, as appropriate. In another method of implanting the convection enhanced delivery system 100 into the patient's tissue, the surgeon or other health care provider may first assemble or construct the entire convection enhanced delivery system by selecting and interconnecting the first, second, third, and fourth convection enhanced delivery devices 110, 210, 310, and 410 to fit the area or space to be treated, such as a resection cavity, and then implant the entire convection enhanced delivery system at one time.

With the first, second, third, and fourth convection enhanced delivery devices 110, 210, 310, and 410 appropriately positioned in the patient's tissue and fluidly interconnected or in fluid communication with one another, therapeutic treatment of the tissue with a bioactive material can begin. The surgeon or other health care provider connects the convection enhanced delivery system 100 to the fluid source 102 using the first external fluid conduit 104 for delivering a fluid, such as a liquid pharmaceutical material, to the convection enhanced delivery system and thus into a patient's tissue. The fluid is delivered from the fluid source 102 into the central lumen of the first external fluid conduit 104. From the first external fluid conduit 104, the fluid containing the bioactive material is delivered through the conduit lumens of the fluid conduits 116, 216, 316, and 416 of the first, second, third, and fourth convection enhanced delivery devices 110, 210, 310, and 410 into the catheter lumens of the microcatheters 114, 214, 314, and 414. The fluid flows along the catheter lumens of the microcatheters 114, 214, 314, and 414 until it reaches the open ends of the distal end portions of the microcatheters and is thereby introduced into the patient's tissue. When the patient's treatment is completed, the convection enhanced delivery system 100 may be removed by disconnecting the first external fluid conduit 104 from the fluid source 102 and the first convection enhanced delivery device 110 and then withdrawing the microcatheters 114, 214, 314, and 414 of the microcatheters 114, 214, 314, and 414 from the patient's tissue.

As a matter of convenience, FIG. 3 shows the first, second, third, and fourth convection enhanced delivery devices 110, 210, 310, and 410 as though the first, second, third, and fourth convection enhanced delivery devices are all implanted in a single, relatively flat tissue surface. Nonetheless, if the convection enhanced delivery system 100 were implanted in, for example, a resection cavity, the first, second, third, and fourth convection enhanced delivery devices 110, 210, 310, and 410 would often be implanted in tissue surfaces that have different orientations relative to one another. In such a situation, the microcatheters 114, 214, 314, and 414 of the convection enhanced delivery devices 110, 210, 310, and 410, respectively, would extend in different directions.

Figure 4:
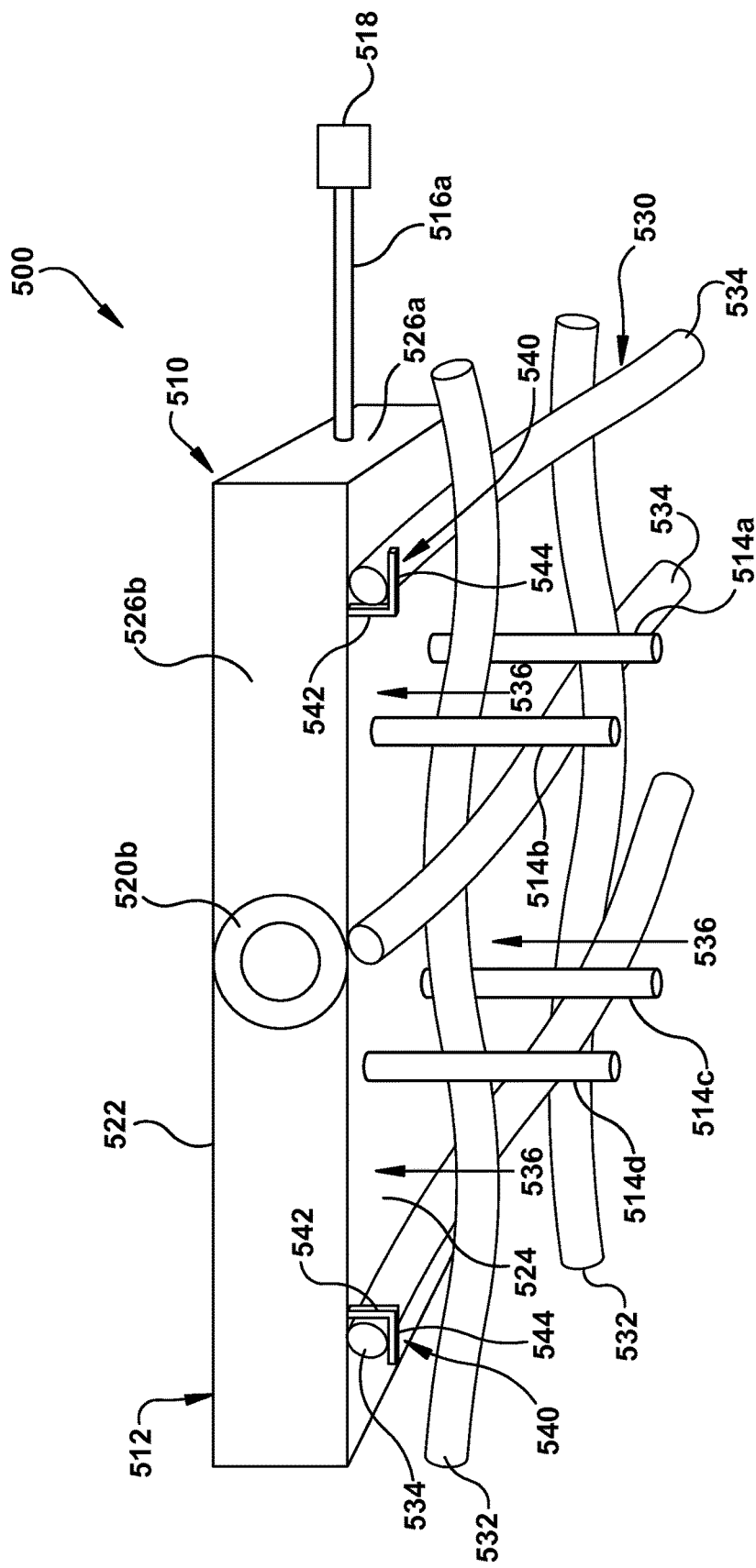
FIG. 4 is a perspective view of a convection enhanced delivery device mounted on a mesh support structure using a first example embodiment of an attachment mechanism in accordance with the present invention.

FIG. 4 illustrates an example of a convection enhanced delivery system 500 that comprises one or more convection enhanced delivery devices 510 mounted on a mesh scaffold or mesh support structure 530. The mesh support structure 530 may be fabricated from a biocompatible polymer, such as medical grade silicone, or from a biocompatible metal. The mesh support structure 530 may be woven, as is shown in FIG. 4, with interwoven, overlying warp and weft filaments or cross members 532 and 534 that define interstices or openings 536 between, for example, four of the cross members. Alternatively, the mesh support structure 530 may be fabricated as a non-woven openwork grid in which the cross members 532 and 534 all lie in a single, common plane and intersect so as to define interstices or openings 536 between the cross members. Each of the openings 536 extends entirely through the mesh structure 530 from an upper surface of the mesh structure to a lower surface of the mesh structure, as viewed in FIG. 4.

The mesh support structure 530 is flexible so that it may be folded, rolled or otherwise formed into a compact package for insertion into an opening in a patient's tissue, such as a resection cavity. The flexibility of the mesh support structure 530 also permits the mesh support structure to be unfolded, unrolled or otherwise unpackaged so that the mesh support structure can be spread out adjacent an exposed surface of a patient's tissue and generally conform to the contours of the exposed surface of the patient's tissue.

The mesh support structure 530 may also be resilient. If the mesh support structure 530 is resilient, it will tend to return to its initial unfolded, unrolled or unpackaged state when it is not constrained or held in a folded, rolled or otherwise packaged condition. The mesh support structure 530, if resilient, will have a self-expanding characteristic and will tend to conform to the contours of the exposed surface of the patient's tissue. Such a resilient mesh support structure 530 will also tend to remain in an expanded or spread-out condition and will resist forces tending to bend, fold or otherwise deform the mesh support structure. The mesh support structure 530 may also include locking mechanisms (not shown) to hold the mesh support structure in an expanded or spread-out condition. Such locking mechanisms may be locked and unlocked or released by the surgeon or other health care provider.

The convection enhanced delivery device 510 shown in FIG. 4 may be the only convection enhanced delivery device used in the convection enhanced delivery system 500 or the convection enhanced delivery device 510 may be one of plural or multiple convection enhanced delivery devices fluidly connected to or in fluid communication with one another in the convection enhanced delivery system 500. Except as described hereafter, the convection enhanced delivery device 510 is identical in shape, dimensions, and construction to the convection enhanced delivery devices 10, 110, 210, 310, and 410 shown in FIGS. 1 to 3. Like the convection enhanced delivery devices 10, 110, 210, 310, and 410, however, the convection enhanced delivery device 510 may include a support member 512 having a different shape and/or different dimensions than the support members 12, 112, 212, 312, and 412 of FIGS. 1-3. Similarly, the convection enhanced delivery device 510 may include a different number of microcatheters 514 with different dimensions than the microcatheters 14, 114, 214, 314, and 414 of the convection enhanced delivery devices 10, 110, 210, 310, and 410, respectively. Further, the convection enhanced delivery device 510 may include different numbers of connecting ports 520 and different numbers, shapes, or flow areas of fluid conduits 516, and/or other differences in construction than the convection enhanced delivery devices 10, 110, 210, 310, and 410.

Unlike the convection enhanced delivery devices 10, 110, 210, 310, and 410, the convection enhanced delivery device 510 includes attachment mechanisms 540 for mounting the convection enhanced delivery device 510 on the mesh support structure 530. Each attachment mechanism 540 has an L-shape with a first leg 542 and a second leg 544. The first leg 542 of each attachment mechanism 540 is secured or bonded, at one end, to the support member 512 and extends in a direction away from and generally perpendicular to the support member 512. The first leg 542 is both flexible and resilient in order to facilitate engaging the attachment mechanism 540 with the mesh support structure 530. The second leg 544 of each attachment mechanism 540 is secured to a distal end of the corresponding first leg 542 and extends in a direction away from and generally perpendicular to the first leg but generally parallel to the support member 512. The second leg 544 is relatively rigid and is secured to the distal end of the first leg 542 so as to (a) to maintain a generally perpendicular orientation with respect to the first leg when the first leg is in a non-flexed or non-deflected condition and (b) thus to facilitate engaging the attachment mechanism 540 with the mesh support structure 530.

The attachment mechanisms 540 are typically arranged in pairs, as is shown in FIG. 4. More particularly, a first attachment mechanism 540 of each pair of attachment mechanisms is secured to the support member 512 so that its second leg 544 extends in a first direction. A second attachment mechanism 540 of each pair of attachment mechanisms is secured to the support member 512 so that its second leg 544 extends in a second direction opposite the first direction. The second leg 544 of the first attachment mechanism 540 may thus pass under and engage with a first cross member 534 of the mesh support structure 530, and the second leg 544 of the second attachment mechanism 540 may similarly pass under and engage with a second cross member 534 that is spaced apart from the first cross member by one or more openings 536 in the mesh support structure 530.

By securing or bonding the first and second attachment mechanisms 540 to the support member 512 so that the first legs 542 of the attachment mechanisms are spaced apart by a predetermined distance corresponding to the distance between two cross members 534, whether or not the cross members are immediately adjacent to or next to one another, the resilience of the first legs 542 will tend to keep the first legs in engagement with the cross members 534. Similarly, the resilience of the first legs 542 and the relative rigidity of the second legs 544, as well as the generally perpendicular orientation between the first and second legs of each attachment mechanism 540, will tend to keep the second legs in engagement with the cross members 534. By spacing the second legs 544 away from the support member 512 by a predetermined distance corresponding to the diameter of a cross member 534, the convection enhanced delivery device 510 will be held on the mesh support structure 530 without shifting either laterally or vertically, as viewed in FIG. 4, relative to the mesh support structure. Although FIG. 4 shows two attachment mechanisms 540 engaging two cross members 534, the attachment mechanisms could alternatively engage two cross members 532. There may also be more than one pair of attachment mechanisms 540 secured to the convection enhanced delivery device 510.

To install the convection enhanced delivery device 510 in the mesh support structure 530 or to mount the convection enhanced delivery device on the mesh support structure, a surgeon or other health care provider may deflect the first legs 542 of the first and second attachment mechanisms 540 of a pair of such attachment mechanisms toward one another. Deflecting the first legs 542 toward one another by a sufficient distance allows the second legs 544 of the first and second attachment mechanisms 540 to pass between two cross members 534 so that the support member 512 of the convection enhanced delivery device 510 may be seated in contact with the mesh support structure 530 and the microcatheters 514 may be inserted into a patient's tissue.

When the convection enhanced delivery device 510 is appropriately positioned relative to the mesh support structure 530, and the microcatheters 514 are appropriately positioned in the patient's tissue, the surgeon or other health care provider may release the first legs 542 of the first and second attachment mechanisms 540 of the pair of attachment mechanisms from their deflected conditions. The resilience of the first legs 542 will cause the first legs to move away from one another and toward the cross members 534. Such movement will cause the first legs 542 to engage or come into contact with the cross members 534 and simultaneously cause the second legs 544 of the attachment mechanisms 540 to move under, as viewed in FIG. 4, the cross members and to engage or come into contact with the cross members. Further, such movement will simultaneously cause the second major surface 524 of the support member 512 to engage or come into contact with the cross members 534.

The convection enhanced delivery device 510 will then be securely and closely mounted on or attached to the mesh support structure 530. The mesh support structure 530 will hold the microcatheters 514 in their desired positions in the patient's tissue. The mesh support structure 530 will be particularly effective in this regard if the mesh support structure is resilient so that it tends to remain in an expanded or spread-out condition and resists forces tending to bend, fold or otherwise deform it. The attachment mechanisms 540 may subsequently be intentionally released or detached or disengaged from the mesh support structure by a surgeon or other health care provider when desired to move the convection enhanced delivery device or to remove the convection enhanced delivery device entirely from the patient. The process of releasing or detaching or disengaging the convection enhanced delivery device 510 from the mesh support structure 530 again involves deflecting the first legs 542 of the pair of attachment mechanisms 540 toward one another so that the attachment mechanisms move out of contact or engagement with the cross member 534 of the mesh support structure.

Figure 5:
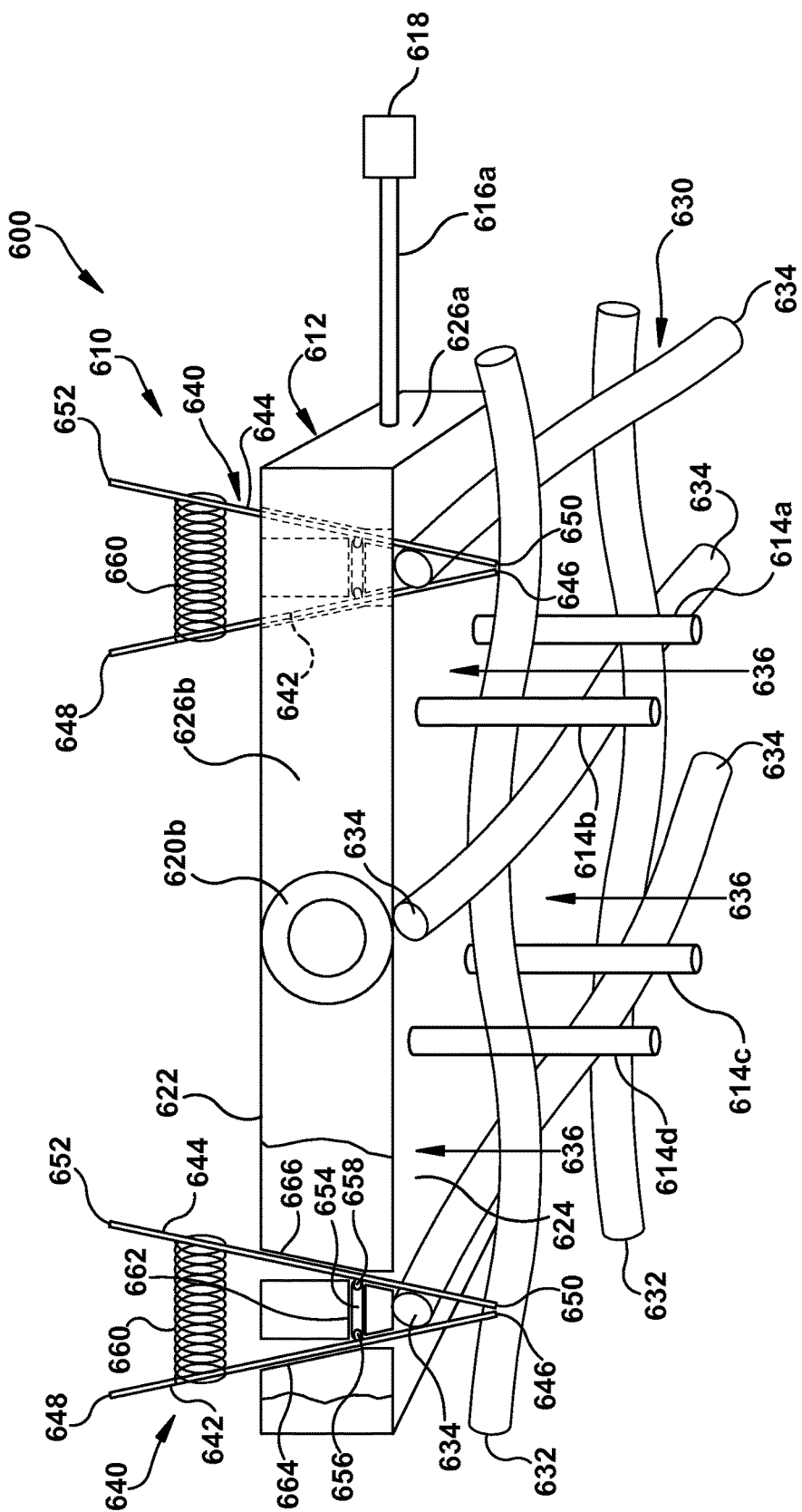
FIG. 5 is a perspective view of a convection enhanced delivery device mounted on a mesh support structure using a second example embodiment of an attachment mechanism in accordance with the present invention.

FIG. 5 illustrates another example of a convection enhanced delivery system 600 that comprises one or more convection enhanced delivery devices 610 mounted on a mesh scaffold or mesh support structure 630. Like the mesh support structure 530, the mesh support structure 630 may be fabricated from a biocompatible polymer, such as medical grade silicone, or from a biocompatible metal. The mesh support structure 630 may be woven, as is shown in FIG. 5, with interwoven, overlying warp and weft filaments or cross members 632 and 634 that define interstices or openings 636 between, for example, four of the cross members. Alternatively, the mesh support structure 630 may be fabricated as a non-woven openwork grid in which the cross members 632 and 634 all lie in a single, common plane and intersect so as to define interstices or openings 636 between the cross members. Each of the openings 636 extends entirely through the mesh structure 630 from an upper surface of the mesh structure to a lower surface of the mesh structure, as viewed in FIG. 5.

The mesh support structure 630 is flexible, like the mesh support structure 530, so that it may be folded, rolled or otherwise formed into a compact package for insertion into an opening in a patient's tissue, such as a resection cavity. The flexibility of the mesh support structure 630 also permits the mesh support structure to be unfolded, unrolled or otherwise unpackaged so that the mesh support structure can be spread out adjacent an exposed surface of a patient's tissue and generally conform to the contours of the exposed surface of the patient's tissue.

The mesh support structure 630 may also be resilient. If the mesh support structure 630 is resilient, it will tend to return to its initial unfolded, unrolled or unpackaged state when it is not constrained or held in a folded, rolled or otherwise packaged condition. The mesh support structure 630, if resilient, will have a self-expanding characteristic and will tend to conform to the contours of the exposed surface of the patient's tissue. Such a resilient mesh support structure 630 will also tend to remain in an expanded or spread-out condition and will resist forces tending to bend, fold or otherwise deform the mesh support structure. The mesh support structure 630 may also include locking mechanisms (not shown) to hold the mesh support structure in an expanded or spread-out condition. Such locking mechanisms may be locked and unlocked or released by the surgeon or other health care provider.

The convection enhanced delivery device 610 shown in FIG. 5 may be the only convection enhanced delivery device used in the convection enhanced delivery system 600 or the convection enhanced delivery device 610 may be one of plural or multiple convection enhanced delivery devices fluidly connected to or in fluid communication with one another in the convection enhanced delivery system 600. Except as described hereafter, the convection enhanced delivery device 610 is identical in shape, dimensions, and construction to the convection enhanced delivery devices 10, 110, 210, 310, 410, and 510 shown in FIGS. 1 to 4. Like the convection enhanced delivery devices 10, 110, 210, 310, 410, and 510, however, the convection enhanced delivery device 610 may include a support member 612 having a different shape and/or different dimensions than the support members 12, 112, 212, 312, 412, and 512 of FIGS. 1-4. Similarly, the convection enhanced delivery device 610 may include a different number of microcatheters 614 with different dimensions than the microcatheters 14, 114, 214, 314, 414, and 514 of the convection enhanced delivery devices 10, 110, 210, 310, 410, and 510, respectively. Further, the convection enhanced delivery device 610 may include different numbers of connecting ports 620 and different numbers, shapes, or flow areas of fluid conduits 616, and/or other differences in construction than the convection enhanced delivery devices 10, 110, 210, 310, 410, and 510.

Like the convection enhanced delivery device 510, but unlike the convection enhanced delivery devices 10, 110, 210, 310, and 410, the convection enhanced delivery device 610 includes attachment mechanisms 640 for mounting the convection enhanced delivery device 610 on the mesh support structure 630. Each attachment mechanism 640 has a V-shape with a first leg 642 and a second leg 644. The first leg 642 of each attachment mechanism 640 has a distal end 646 and a proximal end 648. The second leg 644 of each attachment mechanism 640 has a distal end 650 and a proximal end 652. At a location relatively closer to the distal ends 646 and 650 of the first and second legs 642 and 644, respectively, than to the proximal ends 648 and 652, a short, relatively rigid link 654 extends between the first and second legs. At one end, the link 654 is pivotally connected by a hinge 656 to the first leg 642 of the attachment mechanism 640. At its opposite end, the link 654 is pivotally connected by a hinge 658 to the second leg 644 of the attachment mechanism 640. At a location relatively closer to the proximal ends 648 and 652 of the first and second legs 642 and 644, respectively, than to the distal ends 646 and 650, a coil spring 660 extends between the first and second legs. The coil spring 660 is formed and is attached the first and second legs 642 and 644 such that the coil spring biases the proximal ends 648 and 652 of the first and second legs away from one another. As a result, the coil spring 660 biases the first and second legs 642 and 644 to pivot about the hinges 656 and 658 so that the distal ends 646 and 650 of the first and second legs engage one another and tend to remain in contact with each other. The spring-biased contact between the distal ends 646 and 650 of the first and second legs 642 and 644 facilitates engaging the attachment mechanism 640 with the mesh support structure 630.

Each of the attachment mechanisms 640 is mounted on the support member 612 adjacent its link 654. More specifically, the link 654 extends through a horizontal passage 662 disposed between and generally parallel to the first and second major surfaces 622 and 624 of the support member 612. The ends of the link 654 project into spaced apart vertical passages 664 and 666, each of which extends from the first major surface 622 to the second major surface 624 of the support member. The horizontal passage 662 thus connects the vertical passages 664 and 666. The vertical passages 664 and 666 are wider (in a left to right direction, as viewed in FIG. 5) adjacent the first major surface 622 and narrower adjacent the second major surface 624. The vertical passage 664 receives the first leg 642 of the attachment mechanism 640. The vertical passage 666 receives the second leg 644 of the attachment mechanism 640.

The increasing widths of the vertical passages 664 and 666 in a vertical direction, as viewed in FIG. 5, permit the proximal ends 648 and 652 of the first and second legs 642 and 644 to be moved toward and away from one another to cause movement of the distal ends 646 and 650 away from and toward one another, respectively. As a result, the proximal ends 648 and 652 of the first and second legs 642 and 644 may be pinched or moved toward each other to spread or move the distal ends 646 and 650 away from each other so that a cross member 634 of the mesh support structure 630 may be received between the first and second legs adjacent the spaced apart distal ends. With the cross member 634 between the first and second legs 642 and 644, the proximal ends 648 and 652 of the first and second legs can be released so as to be biased apart by the coil spring 660 and so that the distal ends 646 and 650 are biased together or toward one another. The cross member 634 is thus captured or secured between the first and second legs 642 and 644 of the attachment mechanism 640.

By appropriately determining and fabricating the length of the link 654 between the hinges 656 and 658, the length of the first and second legs 642 and 644 between the hinges and the distal ends 646 and 650 of the first and second legs, and the diameter or width of the cross member 634, the biasing force of the coil spring 660 will tend to keep the first and second legs, as well as the second major surface 624 of the support member 612, in engagement with the cross members 634. The convection enhanced delivery device 610 will thus be held on the mesh support structure 630 without shifting either laterally or vertically, as viewed in FIG. 5, relative to the mesh support structure. Although FIG. 5 shows two attachment mechanisms 640 engaging two cross members 634, the attachment mechanisms could alternatively engage two cross member 632. There may also be more than two attachment mechanisms 640 secured to the convection enhanced delivery device 610. Further, although the distal ends 646 and 650 of the first and second legs 642 and 644 are shown as blunt tips, the distal ends and adjacent end portions of the first and second legs may be angled or curved toward one another to provide a different and potentially more extensive engagement with the cross members 634.

To install the convection enhanced delivery device 610 in the mesh support structure 630 or to mount the convection enhanced delivery device on the mesh support structure, a surgeon or other health care provider may pinch or move the proximal ends 648 and 652 of the first and second legs 642 and 644 of each attachment mechanism 640 toward one another. Pinching or moving the proximal ends 648 and 652 of the first and second legs 642 and 644 of each attachment mechanism 640 toward one another by a sufficient distance allows the distal ends 646 and 650 of the first and second legs 642 and 644 of the attachment mechanism 640 to pass on opposite sides of a cross members 634 so that the support member 612 of the convection enhanced delivery device 610 may be seated in contact with the mesh support structure 630 and the microcatheters 614 may be inserted into a patient's tissue.

When the convection enhanced delivery device 610 is appropriately positioned relative to the mesh support structure 630, and the microcatheters 614 are appropriately positioned in the patient's tissue, the surgeon or other health care provider may release the proximal ends 648 and 652 of the first and second legs 642 and 644 of each attachment mechanism 640 from their deflected or pinched together condition. The bias of the coil spring 660 will cause the distal ends 646 and 650 of the first and second legs 642 and 644 of the attachment mechanism 640 to move toward one another and toward the cross member 634. Such movement will cause the first and second legs 642 and 644 to engage or come into contact with the cross member 634 and simultaneously cause the second major surface 624 of the support member 612 to engage or come into contact with the cross member.

The convection enhanced delivery device 610 will then be securely and closely mounted on or attached to the mesh support structure 630. The mesh support structure 630 will hold the microcatheters 614 in their desired positions in the patient's tissue. The mesh support structure 630 will be particularly effective in this regard if the mesh support structure is resilient so that it tends to remain in an expanded or spread-out condition and resists forces tending to bend, fold or otherwise deform it. The attachment mechanisms 640 may subsequently be intentionally released or detached or disengaged from the mesh support structure by a surgeon or other health care provider when desired to move the convection enhanced delivery device or to remove the convection enhanced delivery device entirely from the patient. The process of releasing or detaching or disengaging the convection enhanced delivery device 610 from the mesh support structure 630 again involves pinching or moving the proximal ends 648 and 652 of the first and second legs 642 and 644 of the attachment mechanism 640 toward one another by a sufficient distance to allow the cross member 634 to pass between the distal ends 646 and 650 of the first and second legs 642 and 644 of the attachment mechanism 640 so that the attachment mechanism moves out of contact or engagement with the cross member 634 of the mesh support structure.

Although the microcatheters 14, 114, 214, 314, 414, 514, and 614 of the convection enhanced delivery devices 10, 110, 210, 310, 410, 510, and 610, respectively, have been described as being introduced into a patient's tissue and then later removed from the patient's tissue, the microcatheters and/or the entirety of each convection enhanced delivery device may be fabricated of a material or materials that can be absorbed by the tissue, thereby reducing or eliminating the requirement physically to remove the catheters from the patient's tissue. In addition, the microcatheters 14, 114, 214, 314, 414, 514, and 614 may be fabricated of an electrically conductive material and electrically insulated with a coating or jacket except at the tips of the distal end portions of the microcatheters. The microcatheters 14, 114, 214, 314, 414, 514, and 614 could thus function as electrodes, conducting electrical signals applied to the proximal end portions of the peripheral catheters to the patient's tissue for therapeutic electrical stimulation. Further, while the microcatheters 14, 114, 214, 314, 414, 514, and 614 and the fluid conduits 16, 116, 216, 316, 416, 516, and 616 have been described above and/or illustrated as tubes having a circular cross-section, the microcatheters and the fluid conduits may be tubes of any cross-sectional shape. Still further, while the fluid conduits 16, 116, 216, 316, 416, 516, and 616 have been described above and/or illustrated as components separate from their corresponding support members 12, 112, 212, 312, 412, 512, and 612, the fluid conduits could be formed by being molded into or drilled into the support members.

It will be appreciated that the convection enhanced delivery devices 10, 110, 210, 310, 410, 510, and 610 may be used to treat both neoplastic and non-neoplastic disorders. Bioactive materials introduced into a patient's tissue using any of the convection enhanced delivery devices 10, 110, 210, 310, 410, 510, and 610 may include, for example, chemotherapeutic materials, viruses, proteins, radiologic materials, growth factors, peptides, and non-radioactive tracer molecules. The convection enhanced delivery devices 10, 110, 210, 310, 410, 510, and 610 may be used in a variety of patient tissues, including, for example, brain tissue, spinal cord tissue, and tissue of any organ.

From the above description of the invention, those skilled in the art will perceive improvements, changes and modifications. Such improvements, changes, and/or modifications within the skill of the art are intended to be covered by the appended claims.

Having described the invention, the following is claimed:

1. A convection enhanced delivery device comprising:
    (a) a flexible support member;
    (b) an elongated first microcatheter carried by the support member, the first microcatheter having a length and projecting lengthwise away from the support member such that a proximal end of the first microcatheter is disposed adjacent the support member and an opposite distal end of the first microcatheter is spaced apart from the support member, the first microcatheter including a first catheter lumen extending in a first direction lengthwise of the first microcatheter;
    (c) a first fluid conduit carried by the support member, the first fluid conduit including a first conduit lumen, the first conduit lumen extending in a second direction different than the first direction, the first conduit lumen being in fluid communication with the first catheter lumen;
    (d) an inlet port carried by the support member, the inlet port being in fluid communication with the first fluid conduit such that fluid supplied to the inlet port is delivered by the inlet port to the first fluid conduit, the inlet port being presented outwardly of and away from the support member in a third direction different than the first direction, the inlet port being configured to engage an end portion of a first external fluid conduit such that fluid is supplied to the inlet port by the first external fluid conduit and such that the first external fluid conduit projects away from the inlet port and from the support member, the inlet port being disposed adjacent a first external surface of the support member presented outwardly of and away from the support member; and
    (e) a connecting port carried by the support member and separate from the inlet port, the connecting port being in fluid communication with the first fluid conduit such that fluid is delivered by the first fluid conduit to the connecting port, the connecting port being presented outwardly of and away from the support member in a fourth direction different than the first direction, the connecting port being configured to engage an end portion of a second external fluid conduit such that fluid delivered to the connecting port is delivered by the connecting port to the second external fluid conduit and such that the second external fluid conduit projects away from the connecting port and from the support member, the connecting port being disposed at or outwardly beyond a second external surface of the support member presented outwardly of and away from the support member.

2. A convection enhanced delivery device according to claim 1 wherein the first fluid conduit is embedded in the support member.

3. A convection enhanced delivery device according to claim 1 wherein the first fluid conduit is formed in the support member.

4. A convection enhanced delivery device according to claim 1 further comprising a second fluid conduit carried by the support member, the second fluid conduit including a second conduit lumen, the second conduit lumen extending in a fifth direction different than the first direction and the second direction, the second conduit lumen being in fluid communication with the first conduit lumen.

5. A convection enhanced delivery device according to claim 1 further comprising
    (f) an elongated second microcatheter carried by the support member, the second microcatheter having a length and projecting lengthwise away from the support member such that a proximal end of the second microcatheter is disposed adjacent the support member and an opposite distal end of the second microcatheter is spaced apart from the support member, the second microcatheter including a second catheter lumen extending in a fifth direction lengthwise of the second microcatheter; and
    (g) a second fluid conduit carried by the support member, the second fluid conduit including a second conduit lumen, the second conduit lumen extending in a sixth direction different than the first direction and the second direction, the second conduit lumen being in fluid communication with the second catheter lumen.

6. A convection enhanced delivery device according to claim 5 wherein the first conduit lumen is in fluid communication with the second conduit lumen.

7. A convection enhanced delivery device according to claim 1 wherein the support member includes a tissue contacting surface, the tissue contacting surface being configured to be positioned in substantially complete surface contact with tissue of a patient.

8. A kit of components for a convection enhanced delivery system comprising at least two convection enhanced delivery devices and at least one external connecting fluid conduit for interconnecting said at least two convection enhanced delivery devices, each convection enhanced delivery device comprising:
    (a) a flexible support member;
    (b) an elongated microcatheter carried by the support member, the microcatheter having a length and projecting lengthwise away from the support member such that a proximal end of the microcatheter is disposed adjacent the support member and an opposite distal end of the microcatheter is spaced apart from the support member, the microcatheter including a catheter lumen extending in a first direction lengthwise of the microcatheter;
    (c) a first fluid conduit carried by the support member, the first fluid conduit including a conduit lumen, the conduit lumen extending in a second direction different than the first direction, the conduit lumen being in fluid communication with the catheter lumen;
    (d) an inlet port carried by the support member, the inlet port being in fluid communication with the first fluid conduit such that fluid supplied to the inlet port is delivered by the inlet port to the first fluid conduit, the inlet port being presented outwardly of and away from the support member in a third direction different than the first direction, the inlet port being configured to engage an end portion of a first external fluid conduit such that fluid is supplied to the inlet port by the first external fluid conduit and such that the first external fluid conduit projects away from the inlet port and from the support member, the inlet port being disposed adjacent a first external surface of the support member presented outwardly of and away from the support member; and
(e) a connecting port carried by the support member and separate from the inlet port, the connecting port being in fluid communication with the first fluid conduit such that fluid is delivered by the first fluid conduit to the connecting port, the connecting port being presented outwardly of and away from the support member in a fourth direction different than the first direction, the connecting port being configured to engage an end portion of the at least one external connecting fluid conduit such that fluid delivered to the connecting port is delivered by the connecting port to the at least one external connecting fluid conduit and such that the at least one external connecting fluid conduit projects away from the connecting port and from the support member, the connecting port being disposed at or outwardly beyond a second external surface of the support member presented outwardly of and away from the support member.

9. A kit of components for a convection enhanced delivery system according to claim 8 further comprising a mesh support structure, the mesh support structure including cross members extending in transverse directions to one another so as to define openings through the mesh support structure, the mesh support structure being configured and dimensioned to support the support member of at least one of the convection enhanced delivery devices while permitting the microcatheter carried by the support member to extend through at least one of the openings defined in the mesh support structure by the cross members.

10. A kit of components according to claim 8 wherein the support member of each convection enhanced delivery device includes a tissue contacting surface, the tissue contacting surface being configured to be positioned in substantially complete surface contact with tissue of a patient.

11. A convection enhanced delivery system comprising:
(a) first, second, and third external fluid conduits;
(b) a first convection enhanced delivery device comprising
    (i) a flexible first support member,
    (ii) an elongated first microcatheter carried by the first support member, the first microcatheter having a length and projecting lengthwise away from the first support member such that a proximal end of the first microcatheter is disposed adjacent the first support member and an opposite distal end of the first microcatheter is spaced apart from the first support member, the first microcatheter including a first catheter lumen extending in a first direction lengthwise of the first microcatheter,
    (iii) a first fluid conduit carried by the first support member, the first fluid conduit including a first conduit lumen, the first conduit lumen extending in a second direction different than the first direction, the first conduit lumen being in fluid communication with the first catheter lumen,
    (iv) a first inlet port carried by the first support member, the first inlet port being in fluid communication with the first fluid conduit such that fluid supplied to the first inlet port is delivered by the first inlet port to the first fluid conduit, the first inlet port being presented outwardly of and away from the first support member in a third direction different than the first direction, the first inlet port engaging an end portion of the first external fluid conduit such that fluid is supplied to the first inlet port by the first external fluid conduit and such that the first external fluid conduit projects away from the first inlet port and from the first support member, the first inlet port being disposed adjacent a first external surface of the first support member presented outwardly of and away from the first support member, and
    (v) a first connecting port carried by the first support member and separate from the first inlet port, the first connecting port being in fluid communication with the first fluid conduit such that fluid is delivered by the first fluid conduit to the first connecting port, the first connecting port being presented outwardly of and away from the first support member in a fourth direction different than the first direction, the first connecting port engaging a first end portion of the second external fluid conduit such that fluid delivered to the first connecting port is delivered by the first connecting port to the second external fluid conduit and such that the second external fluid conduit projects away from the first connecting port and from the first support member, the first connecting port being disposed at or outwardly beyond a second external surface of the first support member presented outwardly of and away from the first support member; and
(c) a second convection enhanced delivery device comprising
    (i) a flexible second support member,
    (ii) an elongated second microcatheter carried by the second support member, the second microcatheter having a length and projecting lengthwise away from the second support member such that a proximal end of the second microcatheter is disposed adjacent the second support member and an opposite distal end of the second microcatheter is spaced apart from the second support member, the second microcatheter including a second catheter lumen extending in a fifth direction lengthwise of the second microcatheter,
    (iii) a second fluid conduit carried by the second support member, the second fluid conduit including a second conduit lumen, the second conduit lumen extending in a sixth direction different than the fifth direction, the second conduit lumen being in fluid communication with the second catheter lumen,
    (iv) a second inlet port carried by the second support member, the second inlet port being in fluid communication with the second fluid conduit such that fluid supplied to the second inlet port is delivered by the second inlet port to the second fluid conduit, the second inlet port being presented outwardly of and away from the second support member in a seventh direction different than the fifth direction, the second inlet port engaging a second end portion of the second external fluid conduit such that fluid is supplied to the second inlet port by the second external fluid conduit and such that the second external fluid conduit projects away from the second inlet port and from the second support member, the second inlet port being disposed adjacent a first external surface of the second support member presented outwardly of and away from the second support member, and
    (v) a second connecting port carried by the second support member and separate from the second inlet port, the second connecting port being in fluid communication with the second fluid conduit such that fluid is delivered by the second fluid conduit to the second connecting port, the second connecting port being presented outwardly of and away from the second support member in an eighth direction different than the fifth direction, the second connecting port engaging an end portion of the third external fluid conduit such that fluid delivered to the second connecting port is delivered by the second connecting port to the third external fluid conduit and such that the third external fluid conduit projects away from the second connecting port and from the second support member, the second connecting port being disposed at or outwardly beyond a second external surface of the second support member presented outwardly of and away from the second support member.

12. A convection enhanced delivery system according to claim 11, wherein the first convection enhanced delivery device further comprises
(vi) an elongated third microcatheter carried by the first support member, the third microcatheter having a length and projecting lengthwise away from the first support member such that a proximal end of the third microcatheter is disposed adjacent the first support member and an opposite distal end of the third microcatheter is spaced apart from the first support member, the third microcatheter including a third catheter lumen extending in a ninth direction lengthwise of the third microcatheter; and
(vii) a third fluid conduit carried by the first support member, the third fluid conduit including a third conduit lumen, the third conduit lumen extending in a tenth direction different than the second direction, the third conduit lumen being in fluid communication with the third catheter lumen.

13. A convection enhanced delivery device according to claim 12 wherein the first conduit lumen is in fluid communication with the third conduit lumen.

14. A convection enhanced delivery system according to claim 11 further comprising a mesh support structure, the mesh support structure including cross members extending in transverse directions to one another so as to define openings through the mesh support structure, the mesh support structure being configured and dimensioned to support at least one of the first and second support members while permitting at least one of the first microcatheter and the second microcatheter carried by said at least one of the first and second support member to extend through at least one of the openings defined in the mesh support structure by the cross members.

15. A convection enhanced delivery system according to claim 14, wherein at least one of the first and second convection enhanced delivery devices also comprises an attachment mechanism configured to attach said at least one of the first and second convection enhanced delivery devices to the mesh support structure, the attachment mechanism including at least one leg configured and dimensioned to directly engage at least one cross member of the mesh support structure.

16. A convection enhanced delivery system according to claim 11 wherein each of the first and second support members includes a tissue contacting surface, the tissue contacting surface being configured to be positioned in substantially complete surface contact with tissue of a patient.

17. A convection enhanced delivery system comprising:
(a) a first convection enhanced delivery device comprising
(i) a flexible first support member,
(ii) an elongated first microcatheter carried by the first support member, the first microcatheter having a length and projecting lengthwise away from the first support member such that a proximal end of the first microcatheter is disposed adjacent the first support member and an opposite distal end of the first microcatheter is spaced apart from the first support member, the first microcatheter including a first catheter lumen extending in a first direction lengthwise of the first microcatheter, and
(iii) a first inlet port carried by the first support member, the first inlet port being in fluid communication with the first microcatheter, the first inlet port being presented outwardly of and away from the first support member in a second direction different than the first direction, the first inlet port being configured to engage an end portion of a first external fluid conduit such that fluid is supplied to the first inlet port by the first external fluid conduit and such that the first external fluid conduit projects away from the first inlet port and from the first support member, the first inlet port being disposed adjacent a first external surface of the first support member presented outwardly of and away from the first support member; and
(b) a mesh support structure, the mesh support structure including cross members extending in transverse directions to one another so as to define openings through the mesh support structure, the mesh support structure being configured and dimensioned to support the first support member of the first convection enhanced delivery device while permitting the first microcatheter carried by the first support member to extend through at least one of the openings defined in the mesh support structure by the cross members.

18. A convection enhanced delivery system according to claim 17, wherein the first convection enhanced delivery device further comprises:
(iv) a first fluid conduit carried by the first support member, the first fluid conduit including a first conduit lumen, the first conduit lumen extending in a third direction different than the first direction, the first conduit lumen being in fluid communication with the first catheter lumen, and
(v) a first connecting port carried by the first support member and separate from the first inlet port, the first connecting port being in fluid communication with the first fluid conduit such that fluid is delivered by the first fluid conduit to the first connecting port, the first connecting port being presented outwardly of and away from the first support member in a fourth direction different than the first direction, the first connecting port being configured to engage a first end portion of a second external fluid conduit such that fluid delivered to the first connecting port is delivered by the first connecting port to the second external fluid conduit and such that the second external fluid conduit projects away from the first connecting port and from the first support member, the first connecting port being disposed at or outwardly beyond a second external surface of the first support member presented outwardly of and away from the first support member.

19. A convection enhanced delivery system according to claim 17, wherein the first convection enhanced delivery device also comprises an attachment mechanism configured to attach the first convection enhanced delivery device to the mesh support structure, the attachment mechanism including at least one leg configured and dimensioned to directly engage at least one cross member of the mesh support structure.

20. A convection enhanced delivery system according to claim 17, further comprising:
(c) a second convection enhanced delivery device comprising
(i) a flexible second support member,
(ii) an elongated second microcatheter carried by the second support member, the second microcatheter having a length and projecting lengthwise away from the second support member such that a proximal end of the second microcatheter is disposed adjacent the second support member and an opposite distal end of the second microcatheter is spaced apart from the second support member, the second microcatheter including a second catheter lumen extending in a third direction lengthwise of the second microcatheter, and
(iii) a second inlet port carried by the second support member, the second inlet port being in fluid communication with the second microcatheter, the second inlet port being presented outwardly of and away from the second support member in a fourth direction different than the third direction, the second inlet port being configured to engage an end portion of a second external fluid conduit such that fluid is supplied to the second inlet port by the second external fluid conduit and such that the second external fluid conduit projects away from the second inlet port and from the second support member, the second inlet port being disposed adjacent a first external surface of the second support member presented outwardly of and away from the second support member,
the mesh support structure being configured and dimensioned to support the second support member of the second convection enhanced delivery device while permitting the second microcatheter carried by the second support member to extend through at least one of the openings defined in the mesh support structure by the cross members.

* * * * *